United States Patent
Janek et al.

[11] Patent Number: 5,935,104
[45] Date of Patent: Aug. 10, 1999

[54] SAFETY MEDICAL SYRINGE WITH RETRACTABLE NEEDLE

[75] Inventors: Gregory A Janek, Conover, Ohio; Morris M Lee, Newark, Del.; Elgene R Gillespie, Canton, Ohio

[73] Assignee: Safety Medical Manufacturing, Incorporated, Bushnell, Fla.

[21] Appl. No.: 09/137,429

[22] Filed: Aug. 21, 1998

[51] Int. Cl.⁶ ............................................. A61M 5/00
[52] U.S. Cl. .................................. 604/110; 604/195
[58] Field of Search .......................... 604/195, 192, 604/198, 110, 187, 263

[56] References Cited

U.S. PATENT DOCUMENTS

| | | | |
|---|---|---|---|
| 4,728,320 | 3/1988 | Chen | 604/110 |
| 4,838,863 | 6/1989 | Allard et al. | 604/110 |
| 4,921,486 | 5/1990 | DeChellis et al. | 604/110 |
| 4,950,241 | 8/1990 | Ranford | 604/110 |
| 4,973,316 | 11/1990 | Dysarz | 604/110 |
| 4,978,343 | 12/1990 | Dysarz et al. | 604/110 |
| 5,000,738 | 3/1991 | LaVallo et al. | 604/110 |
| 5,019,044 | 5/1991 | Tsao | 604/110 |
| 5,024,616 | 6/1991 | Ogle, II | 604/110 |
| 5,049,133 | 9/1991 | Villen Pascual | 604/110 |
| 5,064,419 | 11/1991 | Gaarde | 604/110 |
| 5,180,370 | 1/1993 | Gillespie | 604/110 |
| 5,188,599 | 2/1993 | Botich et al. | 604/110 |
| 5,190,526 | 3/1993 | Murray et al. | 604/110 |
| 5,267,961 | 12/1993 | Shaw | 604/110 |
| 5,389,076 | 2/1995 | Shaw | 604/110 |
| 5,423,758 | 6/1995 | Shaw | 604/110 |
| 5,542,927 | 8/1996 | Thorne et al. | 604/110 |
| 5,769,822 | 6/1998 | McGary et al. | 604/110 |
| 5,800,403 | 9/1998 | Pressly, Sr. et al. | 604/195 |
| 5,843,034 | 12/1998 | Redfern et al. | 604/110 |

*Primary Examiner*—John D. Yasko
*Attorney, Agent, or Firm*—Paul E Milliken; Ray L Weber; Lee A Germain

[57] ABSTRACT

A syringe for giving medical injections which has an internal mechanism for releasing and retracting a needle into the syringe after the injection has been given and retaining the needle and a hollow plunger inside the barrel of the syringe to reduce the risk of accidental needle sticks. The interior of the hollow plunger is initially hydraulically sealed off by a plunger front end wall from the fluid chamber of the syringe to prevent fluid from entering the interior of the hollow plunger. After the plunger has been depressed to expel fluid from the barrel, further depression of the plunger causes cutting punch type members to sever a disc shaped flange portion of a stem type needle retaining member and the plunger front end wall thereby permitting the spring to propel the needle and needle retaining member into the hollow plunger thereby retracting the needle and retaining member inside the barrel.

45 Claims, 6 Drawing Sheets

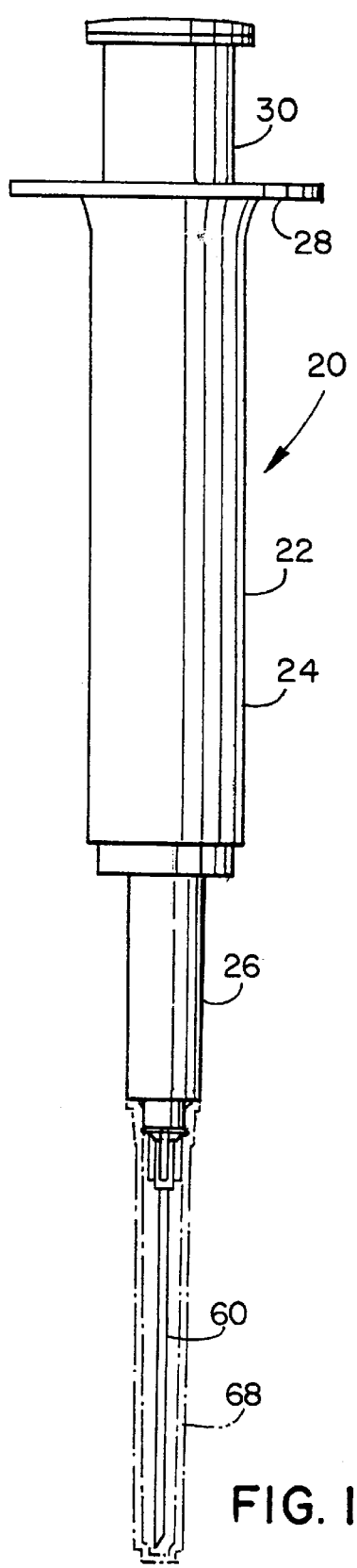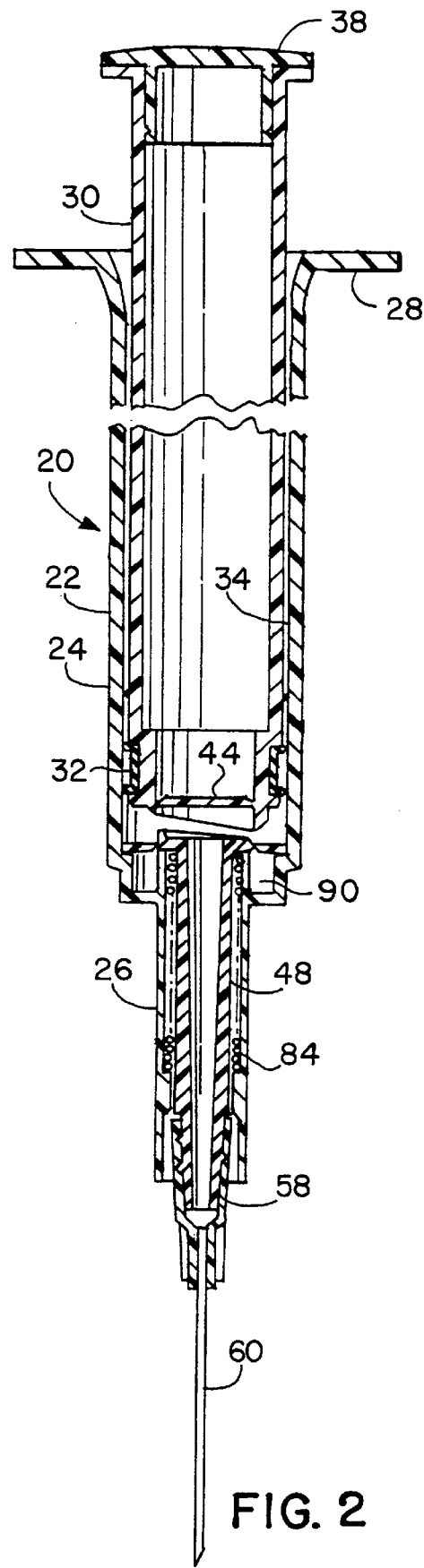
FIG. 1
FIG. 2

SAFETY MEDICAL SYRINGE WITH RETRACTABLE NEEDLE

FIELD OF THE INVENTION

This invention relates generally to medical syringes such as hypodermic syringes and in particular to the type having retractable needles which are withdrawn or propelled into the barrel and/or plunger after an injection has been given, thereby preventing accidental needle sticks which could transmit AIDS, hepatitis and other infectious diseases.

BACKGROUND OF THE INVENTION

In the past various attempts have been made to design hypodermic syringes with retractable needles. Typical examples of such devices are shown in U.S. Pat. Nos. 4,838,863; 5,019,044; 5,064,419; 4,950,241; and 4,978,343.

Some of these patents show the needle retracted into a hollow piston or barrel of a syringe either manually or by a spring which is biased to move the needle into a stored position either within a hollow piston or at least within the barrel of a hypodermic syringe. Such devices are only as effective and reliable as the design of the mechanisms used to retract the needle and some mechanisms may either fail to retract the needle completely or may fail to retain the needle in a retracted position.

The present invention is a further development of the concept shown in prior U.S. Pat. No. 5,180,370 issued to E R Gillespie which uses a hollow plunger in a medical syringe as a needle storage compartment when the needle has been retracted inside the syringe after an injection has been given. One primary advantage of the hollow plunger is that the needle can be in the stored or retracted position inside the plunger when the plunger is pressed into the barrel. In other patents which do not show a hollow plunger, the plunger must either be left protruding from the rear end of the barrel after needle retraction or in some instances the protruding portion of the plunger is broken off at the rear end of the barrel. Either option is not as desirable as having substantially all of the plunger contained inside the barrel after the needle has been retracted.

Both the prior Gillespie patent (U.S. Pat. No. 5,180,370) and the present invention provide a positive means of hydraulically sealing off the interior of the hollow plunger from the fluid chamber of the syringe.

The prior Gillespie patent mentioned above, uses a rupturable end cover member over the front end of the plunger to seal off the interior of the hollow plunger from the fluid chamber and an annular cutting surface to rupture or separate the cover member from the plunger while releasing a needle retaining member to permit the retaining member with a needle to be transmitted into the hollow interior of the plunger.

The present invention uses a positive and realiable end closure cover for sealing off the interior of the plunger from the fluid chamber and an improved angled cutting edge for shearing off and cutting loose the end closure cover or wall and an improved angled cutting edge on the front end of the plunger for shearing or cutting loose the needle retaining assembly from the barrel so that it is propelled by a bias means into the hollow interior of the plunger and retained therein.

Many additional patents have been issued on retractable needles since the prior Gillespie patent. Typical examples of such patents are U.S. Pat. No. 5,188,599 (Botich et al.); U.S. Pat. No. 5,190,526 (Murray et al); and three U.S. Pat. Nos., 5,267,961; 5,389,076; and 5,423,758 (all of which are issued to T R Shaw). The present invention differs from these patents in both the manner in which the end of the plunger is closed and in the manner in which the needle is retained in the front end of the barrel and released therefrom upon depression of the plunger.

OBJECTS OF THE INVENTION

It is a primary object of this invention to provide a hypodermic syringe with a retractable needle which is simple, reliable, will retract rapidly and which will securely retain the needle in the retracted position.

Another object of this invention is to provide a hypodermic syringe with a retractable needle wherein the plunger or piston remains in a depressed position within the barrel of the syringe after the needle is retracted into the plunger.

Another object of the invention is to provide a hypodermic syringe which has a positive and reliable release means to ensure needle release from the barrel to permit needle retraction into a needle receiving chamber in the plunger of the syringe.

A still further object of this invention is to provide a hypodermic syringe with a retractable needle which is inexpensive to manufacture and easy to use.

An even further object of this invention is to provide a hypodermic syringe with a retractable needle in which various sizes of needles are readily interchangeable with the same barrel.

These and other objects of the invention will become more fully apparent in the following specification and the attached drawings.

SUMMARY OF THE INVENTION

A safety syringe comprising: a hollow barrel for containing a fluid having a cylindrical wall, a rear end opening and a front end opening and a fluid chamber therein extending between said openings, a hollow plunger mounted in the fluid chamber of the barrel and axially moveable back and forth between the front and rear end opening of the barrel, for the intake and expulsion of fluid from the fluid chamber, the plunger containing an axial needle receiving chamber therein and the plunger having a rear end portion extending out of the rear end opening of the barrel, a sealing means extending around the periphery of the plunger, engaging an inside surface of the wall of the barrel within the fluid chamber to prevent fluid from leaking out of the rear end of the barrel, a barrier means sealingly attached to the plunger adjacent the front end thereof to hydraulically separate the needle receiving chamber from the fluid chamber to prevent fluid from the fluid chamber from entering the needle receiving chamber, a hollow needle temporarily sealingly mounted at the front end of the barrel and protruding therefrom, the fluid chamber being in communication with the interior of the hollow needle to permit fluid to flow from the fluid chamber through the needle when the plunger is moved toward the front end of the barrel, needle retaining means sealingly attached to the barrel and the needle for holding the needle in a forwardly extended position until fluid has been expelled from the fluid chamber, bias means within the barrel associated with the needle retaining means urging the needle and the needle retaining means rearwardly in the barrel and toward a retracted position in the interior of the needle receiving chamber, a first annular punch type release means on the front end of the plunger and adapted to rupture the needle retaining means for releasing it from the barrel to permit the bias means to move the needle and needle retaining means toward the needle receiving chamber after the fluid has been expelled from the fluid chamber, and a second annular punch type release means extending rearwardly from the rear end of the needle retaining means to rupture the barrier means and open the front end of the plunger to receive the needle and needle retaining means into the needle receiving chamber.

DESCRIPTION OF THE DRAWINGS

FIG. 1 is a side elevational view of the syringe of this invention;

FIG. 2 is an axial cross-sectional view of the syringe of FIG. 1 illustrating the various working parts of the invention with the plunger substantially depressed and the needle protruding from the front end of the barrel;

DESCRIPTION OF THE PREFERRED EMBODIMENTS

Figure 3:
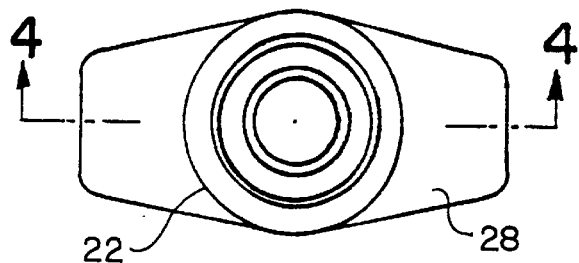
FIG. 3 is an enlarged rear end view of the barrel of the syringe of FIG. 2.

Referring now to the drawings and in particular to FIGS. 1 and 2, a medical syringe is indicated generally by the numeral 20. The syringe 20 has a hollow cylindrical barrel 22 (also shown in FIG. 3) which is open at the rear end and has a main body portion 24 and a hollow front end extension 26 of reduced diameter from the body portion 24. The barrel also has transverse flanges 28 at the rear end thereof which are gripped by the fingers of a user of the syringe 20.

Figure 5:
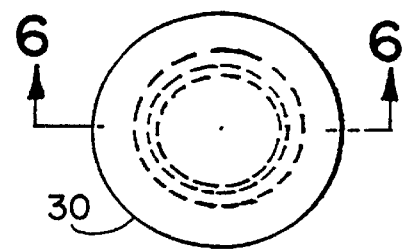
FIG. 5 is an enlarged rear end view of the hollow plunger of the syringe of FIG. 2.

A hollow plunger 30 (also shown in FIGS. 5 and 6) is inserted into the open rear end of the barrel 22 and is axially slideable therein. The plunger 30 has a resilient seal 32 encircling the plunger near the front end and sealing against an inner surface 34 of the barrel main body portion 24. The seal 32 fits in an annular groove 36 (shown in FIG. 6) near the front end of the plunger 30. Both the barrel 22 and the plunger 30 as well as the other later described parts of the syringe 20 are made preferably of radiation resistant thermoplastic material such as Polypropylene or the like by injection and coining molding or injection and compression molding or extrusion and compression molding of multiple cavities rotary stations.

Figure 6:
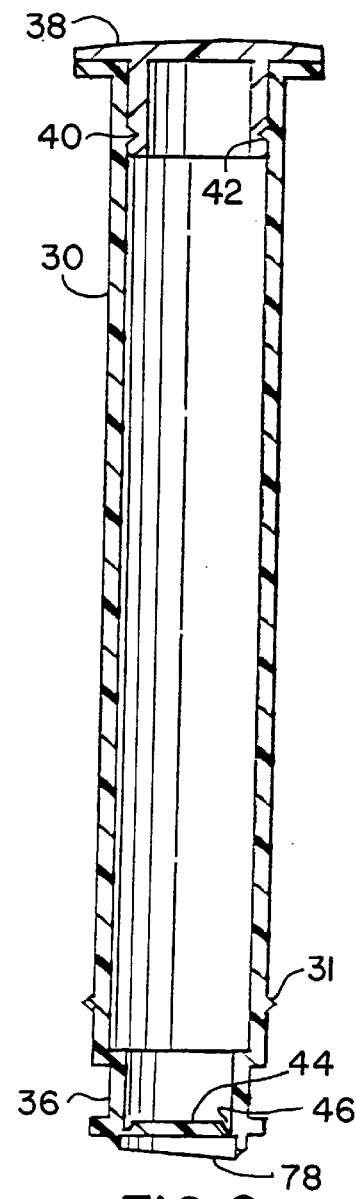
FIG. 6 is an enlarged axial cross-sectional view of the hollow plunger of the syringe taken on line 6—6 of FIG. 5.

The plunger 30 has a rear end cap 38 which is snapped in place by means of an annular groove 40 which receives an annular rib 42 (shown in FIG. 6).

Figure 4:
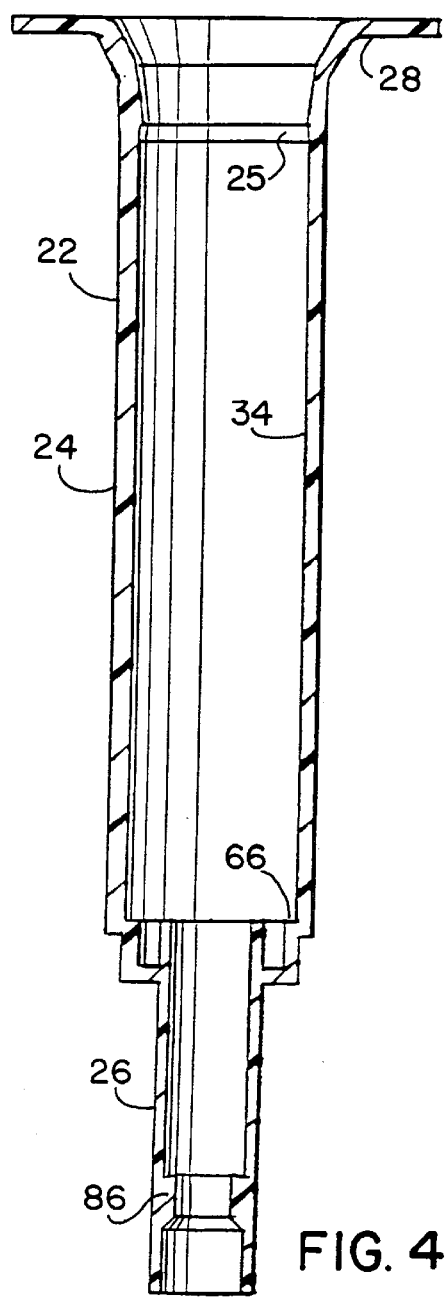
FIG. 4 is an enlarged axial cross-sectional view of the barrel of the syringe taken on line 4—4 of FIG. 3.

The plunger 30 has an annular rib or protrusion 31 which holds the plunger in centered axial alignment within the barrel 22. This rib 31 also serves to prevent the plunger 30 from being pulled out of the barrel 30 if the rib comes in contact with a reduced diameter portion 25 near the rear end of the barrel 22 as shown in FIG. 4.

The front end of the hollow plunger 30 is sealingly closed by a disc shaped end wall 44 which is preferably molded as an integral part of the plunger 30. The end wall 44 has an annular notch 46 extending around the periphery thereof which provides a thin membrane portion and a notch effect which makes the wall 44 easier to sever from the plunger as will be explained later.

Figure 7:
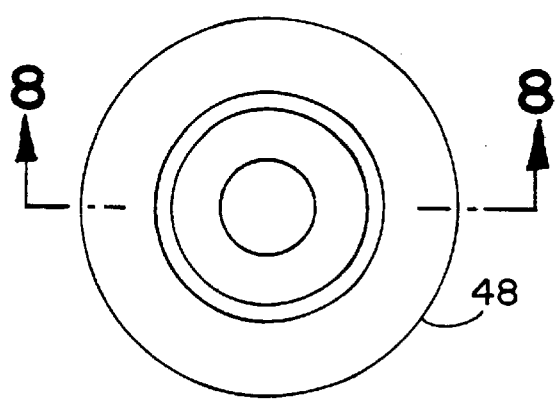
FIG. 7 is an enlarged rear end view of a hollow stem which is separably attached adjacent to the front end of the syringe barrel.
Figure 8:
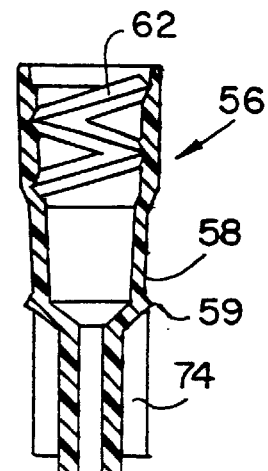
FIG. 8 is an enlarged axial cross-sectional view of the hollow stem taken on line 8—8 of FIG. 7.
Figure 8:
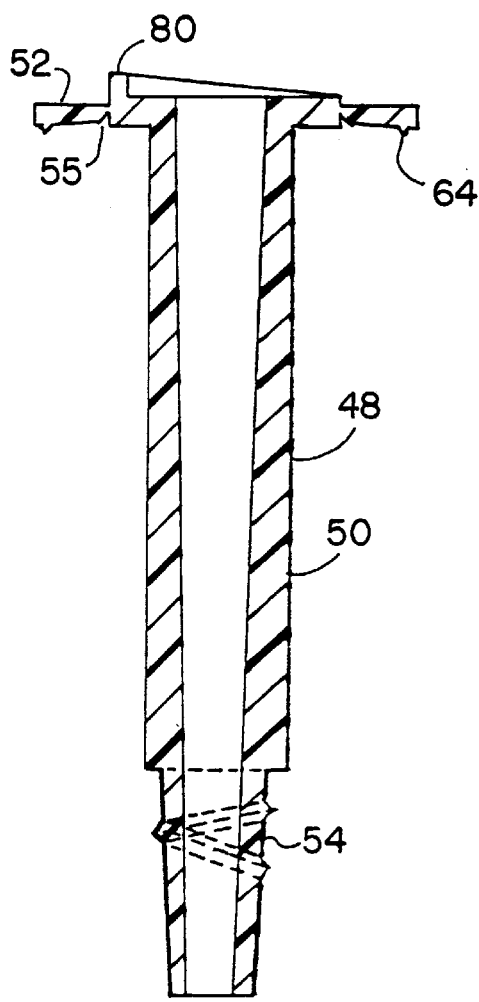

Referring now to FIGS. 7 and 8 is a hollow stem 48 having a tubular body portion 50, a radially outwardly extending annular flange or disc 52 molded integrally on the rear end of the stem 48, and a threaded portion 54 on the front end thereof.

The flange 52 has an annular notch 55 which is similar to the notch 46 in the end wall 44 and produces an annular membrane and a notch effect. This notch 55 and the notch effect makes it easier for the stem 48 to be severed from the barrel 22 and release the stem 48 from the barrel 22. As an alternative, the annular notches 46 and 55 and their notch effect can be placed on the opposite side of the respective part on which they are shown in the drawings. The main objective of the notches is to provide a thin membrane portion and notch effect which is easy to sever when the plunger 30 is depressed. The notches 46 and 55 are circumferentially aligned with the annular cutting edges 78 and 80 so that the cutting edges pass through the thin membranes when cutting is performed.

Figure 9:
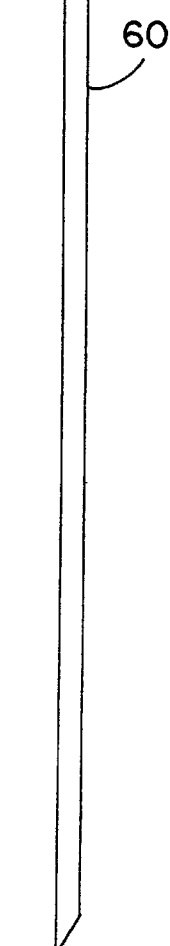
FIG. 9 is an enlarged axial cross-sectional view of an assembly of a needle mounted in a hub.

Referring now to FIG. 9 is a needle assembly 56 comprising a needle hub 58 to which is attached a needle 60 by suitable bonding adhesive. The hub 58 has a threaded portion 62 which engages the threaded portion 54 on the stem 48. The threads in the present example are inclined at a steep angle and are commonly know as a "Luer-Lok" configuration. The needle and hub assembly 56 is screwed onto the stem 48 which in turn is attached to the barrel 22 preferably by ultrasonic bonding. Annular ridge 64 on the flange 52 makes contact with ledge 66 to permit ultrasonic bonding of the stem 48 to the barrel 22.

Figure 10:
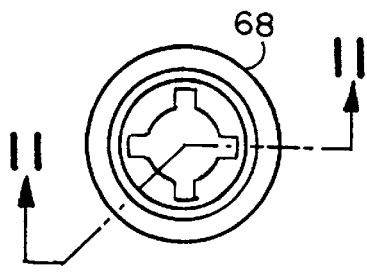
FIG. 10 is an enlarged rear end view of a hollow needle cap which fits over the needle and snaps onto the hub of FIG. 9.
Figure 11:
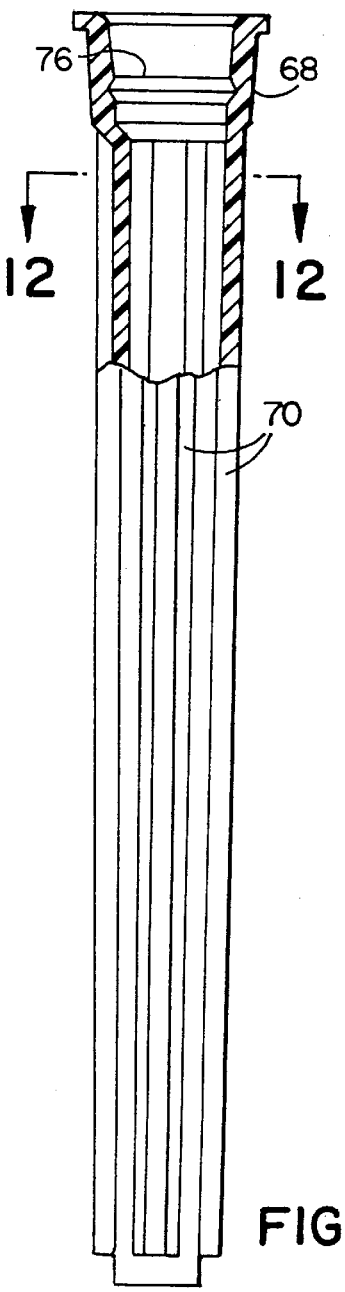
FIG. 11 is an enlarged partially broken away axial cross-sectional view of the hollow needle cap taken on line 11—11 of FIG. 10.
Figure 12:
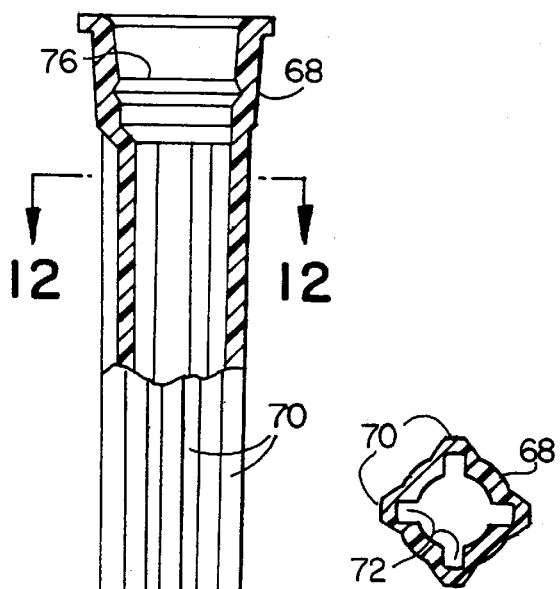
FIG. 12 is a cross-sectional view of the needle cap taken on line 12—12 of FIG. 11.
Figure 13:
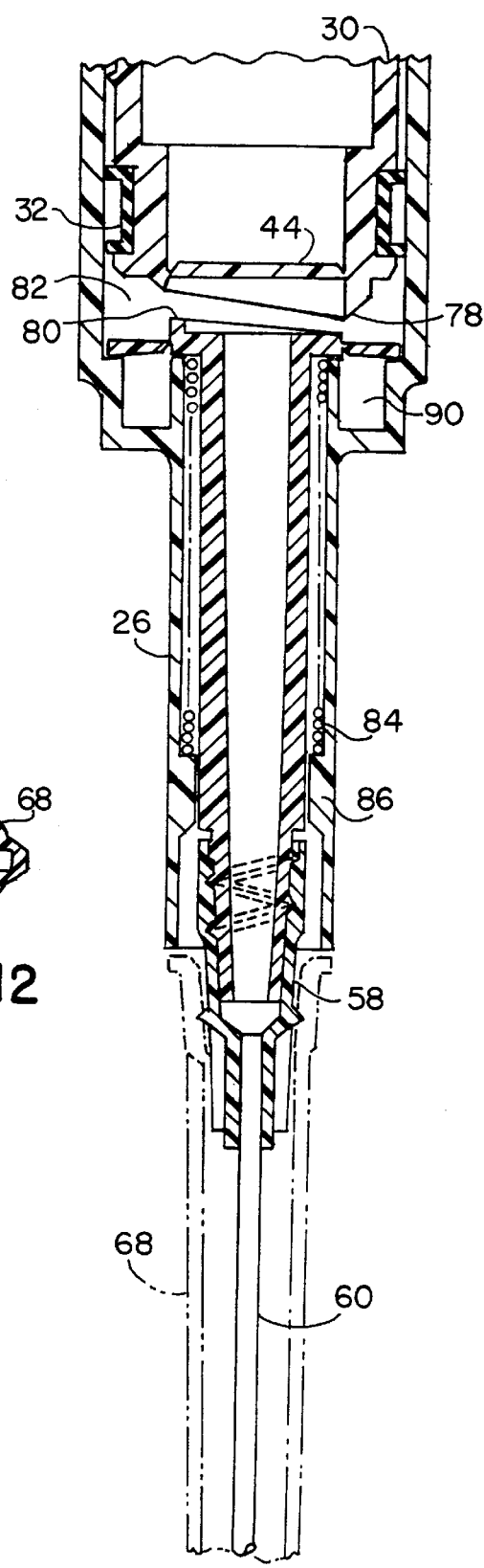
FIG. 13 is a enlarged cross-sectional partial view of the syringe shown in FIG. 2 to better emphasize the release mechanism for causing the stem and needle assembly to be released into the hollow plunger.

It should be noted at this point that a sheath or cap 68 as shown in FIGS. 10 through 12 is shown in chain dotted lines in FIGS. 1 and 13 snapped onto an annular ridge 59 on the needle hub 58. The sheath 68 has ribs 70 which makes it easy to grasp and rotate when screwing the needle assembly 56 onto the stem 48.

As shown in FIG. 12, the sheath has a plurality of longitudinal grooves 72 inside the ribs 70. The grooves 72 are positioned to match with a plurality of fins 74 extending radially outwardly from the hub 58 as shown in FIG. 9. When the sheath 68 is snapped onto the hub 58 an annular inwardly facing groove 76 near the rear end of the sheath 68 snaps over the ridge 59 on the needle hub 58 and holds it in place. The engagement of the fins 74 and the grooves 72 permits the sheath 68 and the needle assembly 56 to be rotated together as a unit to screw the needle assembly 56 onto the threaded portion 54 of the stem 48. The interior of the needle hub 58 has a threaded portion 62 which engages the threaded portion 54 of the stem 48.

It may be seen that various sizes of needles can be interchangeable by selecting and attaching the desired size of needle assembly 56 to the stem 48.

FIG. 13 shows an enlarged version of the syringe 20 shown in FIG. 2 with the plunger 30 approaching the flange 52 of the stem 48.

At this point it should be noted that the plunger 30 on the front end thereof has a sharp annular cutting edge 78 on the plunger 30 which severs the flange 52 of the stem 48 when the plunger 30 is depressed to a certain position. Likewise the flange 52 of the stem 48 has a cutting edge 80 which severs the wall 44 of the plunger 30.

The cutting edges 78 and 80 are both inclined at an angle of approximately 5 degrees to a plane which is perpendicular to the axis of the syringe 20. This angle of inclination is necessary to provide a pointed force and shearing action on both the plunger end wall 44 and the flange 52 when the plunger 30 is depressed forwardly beyond a certain distance.

In operation FIG. 13 shows the plunger 30 as the forward end approaches the front end of the barrel main body 24. Assuming that a liquid medication has been drawn into a liquid chamber 82 between the barrel 22 and the plunger 30, as the plunger 30 approaches the front end of the barrel main body 24, most of the liquid medication has been injected into the patient.

Figure 14:
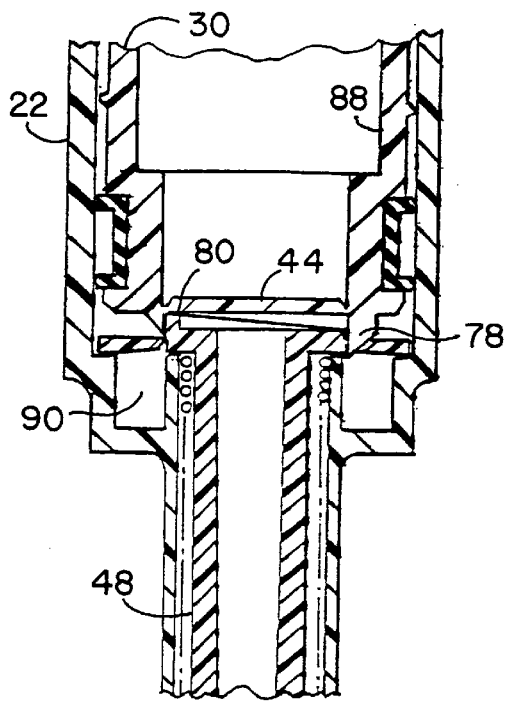
FIG. 14 is an enlarged fragmentary cross-sectional view similar to FIG. 13 with the plunger moved axially forward a sufficient distance that the end of the plunger is starting to sever the stem from the barrel.

As the plunger 30 is depressed further forward, the cutting edge 78 on the front end of the plunger 30 contacts and severs the flange 52 thereby releasing the stem 48 and permitting it to be propelled rearwardly by a compression spring 84 as shown in FIG. 14. As may be seen in FIG. 13, before release of the stem 48, the spring 84 is held under compression between the flange 52 on the stem 48 and an annular retaining band 86 which is formed as a thickened portion on the inside of the front end extension 26.

Figure 15:
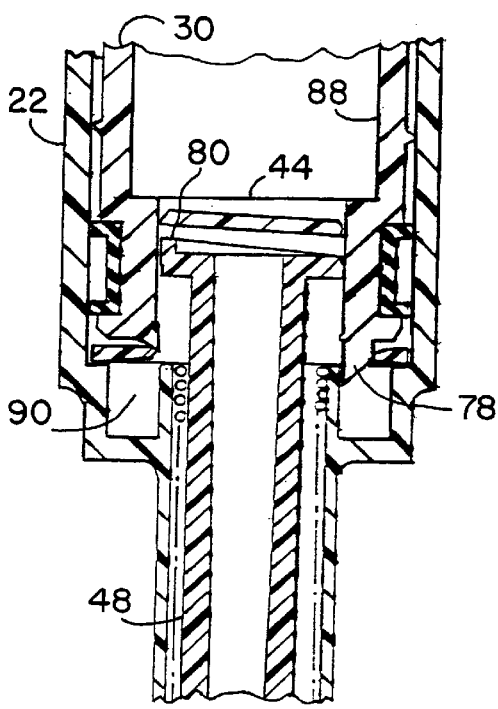
FIG. 15 is an enlarged fragmentary cross-sectional view similar to FIG. 14 but with the plunger moved axially forward even farther so that the rear end of the stem has severed a front end wall of the hollow plunger and the stem has started to move into the plunger.
Figure 16:
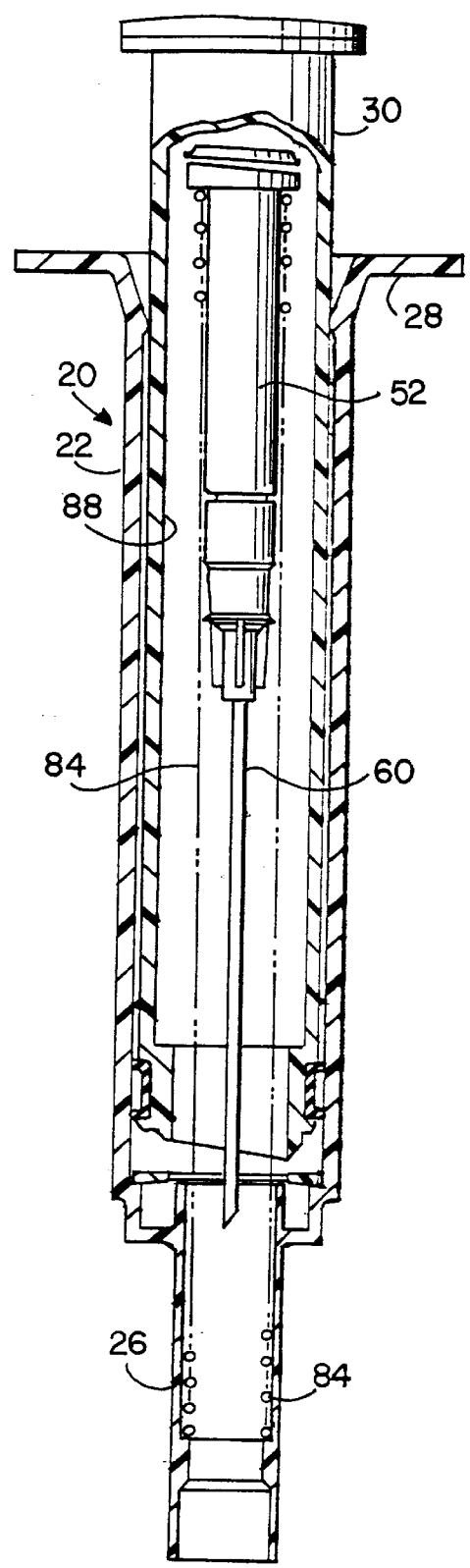
FIG. 16 is a cross sectional view of the syringe of the invention similar to FIG. 2 but showing the stem and needle assembly fully enclosed in the plunger and barrel and held in the retracted position by a compression spring.

Immediately after the plunger severs the flange 52, the cutting edge 80 on the rear end of the flange 52 severs the front end wall 44 from the plunger 30 and permits the stem 48 and the needle assembly 56 to be propelled rearwardly by the compression spring 84 into the hollow interior 88 of the plunger 30 as shown in FIG. 15 where it comes to rest inside the hollow interior 88 of the plunger 30 as shown in FIG. 16 where it is held in a retracted position by the spring 84. As the plunger 30 is depressed to sever the stem flange 52 the cutting edge 78 can enter an annular channel 90 which provides clearance for easier forward movement of the plunger 30 and easier deflection of the flange 52 and also receives any remaining liquid medication from the liquid chamber 82.

It should be recognized that the important components which cause the release of the stem 48 and needle assembly 56 and the plunger end wall 44 are the cutting edges 78 and 80 and the notch effect at the annular notches 46 and 55. These edges cooperate to permit the retraction of the needle 60 by being propelled rearwardly by the spring 84. The inclined plane in which the edges 78 and 80 lie is the primary reason that these edges create a pointed force and shearing action on the disk 52 and the wall 44 and in which the notch effect is provided on the notches 46 and 55, thereby providing a more positive and reliable release and retraction of the needle assembly 56 and stem 48. It can be seen that the annular cutting edge 80 telescopes inside the annular cutting edge 78, and in the embodiment showing in FIGS. 2 through 16, this results in the severing of the stem disk 52 slightly before severing of the plunger end wall 44.

Figure 17:
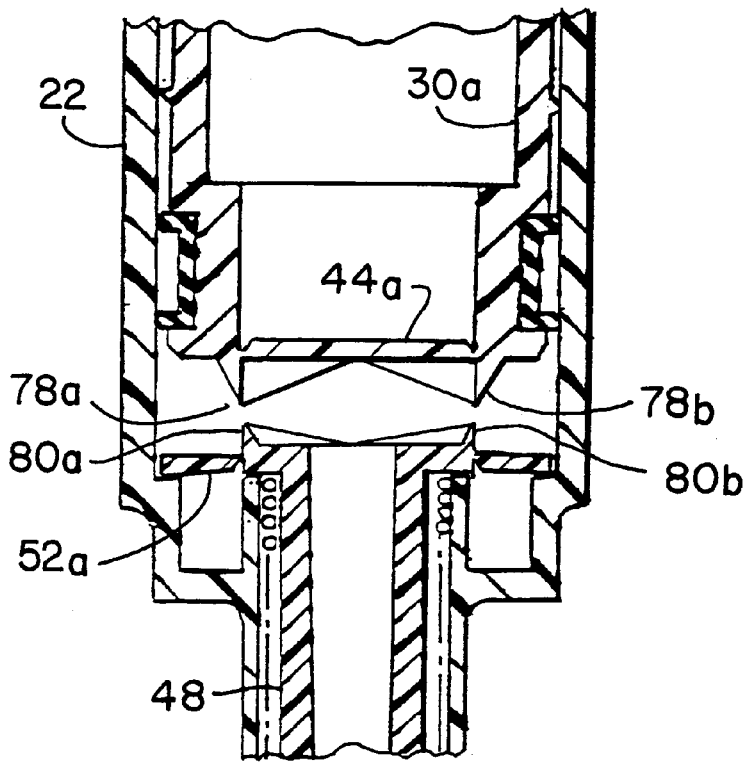
FIG. 17 is an enlarged fragmentary axial cross section similar to FIGS. 14 and 15 but showing another embodiment of the stem and needle assembly release mechanism having multi-angled cutting edges.

Referring now to FIG. 17, another embodiment of the invention shows multi-angle cutting edges 78a and 78b on the plunger 30a and multi-angle cutting edges 80a and 80b on the stem disk 52a. These cutting edges perform the same function as the cutting edges 78 and 80 but with a different angle configuration.

Figure 18:
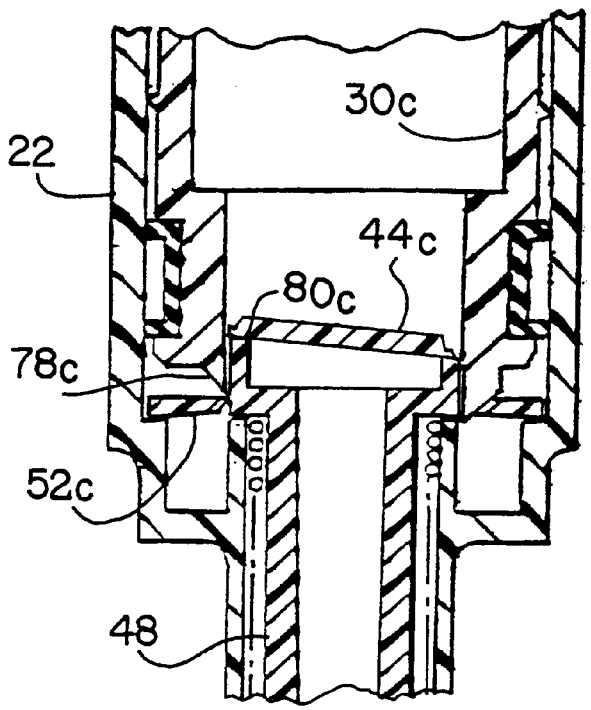
FIG. 18 is an enlarged fragmentary axial cross section similar to FIGS. 14 and 15 but showing still another embodiment of the stem and needle assembly release mechanism which is designed to sever the plunger end wall before severing the stem from the barrel.

Another embodiment shown in FIG. 18 shows cutting edges 78c and 80c in which the axial length of the stem mounted cutting edge 80c is longer than cutting edge 78c on the plunger 30c. This causes the end wall 44c to be severed and released before the disk 52c.

It can be seen that other needle release and retraction means can be used without departing from the scope of the inventions as long as the syringe uses a hollow plunger with a means of hydraulically sealing off the interior of the plunger from the fluid chamber of the syringe.

It should also be recognized that the detailed contours and proportions of the various components such as the needle holding components and cutting edges can vary from some of the illustrations shown in the drawings and the components can be made from various alternative materials from those disclosed herein without departing from the scope of the invention. These and various other modifications can be made in the embodiments shown and described herein without departing from the scope of the invention.

We claim:

1. A safety syringe comprising:

a hollow barrel for containing a fluid having a cylindrical wall, a rear end opening and a front end opening and a fluid chamber therein extending between said openings;

a hollow plunger mounted in the fluid chamber of the barrel and axially moveable back and forth within the barrel, for the intake and expulsion of fluid from the fluid chamber, the plunger containing an axial needle receiving chamber therein, used during needle retraction and the plunger having a rear end portion extending out of the rear end opening of the barrel and a front end portion positioned inside the barrel;

sealing means extending around the periphery of the plunger, engaging the inside surface of the wall of the barrel within the fluid chamber to prevent fluid from leaking out of the rear end of the barrel;

a first rupturable disc sealingly temporarily closing the needle receiving chamber of the plunger adjacent the front end thereof to prevent fluid from the fluid chamber from entering the needle receiving chamber;

a needle retaining member having a front end and rear end and having a second rupturable disc member at the rear end thereof sealingly attached to the barrel until fluid has been expelled from the fluid chamber;

a hollow needle sealingly mounted in the needle retaining member at the front end of the barrel and protruding therefrom, a rear end of the needle in communication with the fluid chamber to permit the flow of fluid from the fluid chamber through the needle;

a first annular punch type release means on the front end of the plunger and adapted to rupture the second disc member on the needle retaining means for releasing it from the barrel after the fluid has been expelled from the fluid chamber;

a second annular punch type release means extending rearwardly from the second disc member at the rear end of the needle retaining member to rupture the first rupturable disc and open the front end of the plunger to receive the needle and needle retaining member into the needle receiving chamber;

both the first and second punch type release means having a sharp leading edge inclined at an angle to both the rupturable discs, so that each leading edge, when penetrating its respective disk, creates a pointed force and shearing action to separate each rupturable disc respectively from either the barrel or the plunger; and bias means within the barrel associated with the needle retaining member urging the needle and the needle retaining member rearwardly in the barrel and toward a retracted position in the interior of the needle receiving chamber.

2. A safety syringe as claimed in claim 1 wherein the bias means is a compression spring within the barrel at the front end thereof.

3. A safety syringe as claimed in claim 2 wherein the needle retaining member has an elongated tubular stem fixedly attached to the second rupturable disc member.

4. A safety syringe as claimed in claim 3 wherein the compression spring surrounds the stem and is maintained under compression between the second rupturable disc and a ledge of the barrel.

5. A safety syringe as claimed in claim 4 including a needle hub attached to the front end of the stem and having the needle axially secured therein.

6. A safety syringe as claimed in claim 1 wherein at least one of the rupturable discs has a circular notch in axial alignment with one of the annular punch type release means to permit the disc to be ruptured with less pressure of the plunger.

7. A safety syringe as claimed in claim 6 wherein both of the rupturable discs has a circular notch creating a thin membrane and notch effect to permit easier rupture of the discs.

8. A safety syringe as claimed in claim 2 wherein the compression spring is adapted to retain the needle and needle retaining member within the needle receiving chamber of the plunger and in the barrel after retraction of the needle.

9. A safety syringe as claimed in claim 1 wherein the angle of inclination of the leading edge of the release means relative to the respective rupturable disc is at least 5°.

10. A safety syringe as claimed in claim 1 wherein the leading edge of both the punch type release means has multiple angles.

11. A safety syringe as claimed in claim 1 wherein both the first and second punch type release means has a sharp leading edge inclined at an angle to provide application of a pointed load force sequentially to rupturable membrane portions on both the first and second rupturable discs to reduce the amount of plunger force needed to rupture the discs.

12. A safety syringe as claimed in claim 1 wherein a leading edge of both the punch type release means has a recessed angle across its wall section preferably at 45° assuring sharp leading edge and highest point at the inside diameter of the release means on the front end of the plunger and at the outside diameter of the needle retaining member release means and located as close to the disc notch membrane to facilitate disc rupture during release of the needle.

13. A safety syringe as claimed in claim 1 wherein the axial length of one of the release means is greater than that of the other to provide sequential rupturing of the first and second rupturable discs.

14. A safety syringe as claimed in claim 13 wherein the first release means is of greater axial length than the second release means to cause rupture of the second disc member before rupture of the first disc member.

15. A safety syringe as claimed in claim 1 wherein the needle retaining member includes a hollow stem temporarily attached to the barrel and the needle secured in a needle hub which is removably attached to the stem by a twist lock means thereby permitting interchangability of different sizes of needles on the stem.

16. A safety syringe as claimed in claim 15 wherein the twist lock means includes a high pitch reversed "Luer Lok" type thread on the outside diameter of the stem at the front end thereof and protrudes out of the front of the barrel and a matching high pitch reversed "Luer Lok" type thread on the inside diameter of the needle hub for rapid engagement with the stem by rotating the hub relative to the stem.

17. A safety syringe as claimed in claim 16 including a needle cap having radially inwardly facing grooves which match with radially outwardly extending fins on the needle hub and having ribs on the outside surface of the needle cap to permit ease of rotation of the needle cap and needle hub when attaching or removing the needle hub and needle from the stem.

18. A safety syringe comprising:

a hollow barrel for containing a fluid having a cylindrical wall, a rear end opening and a front end opening and a fluid chamber therein extending between said openings;

a hollow plunger mounted in the barrel and axially moveable back and forth within the barrel, for the intake and expulsion of fluid from the barrel, the plunger containing an axial needle receiving chamber therein, used during needle retraction;

sealing means extending around the plunger, and slidably engaging an inside surface of the wall of the barrel to prevent fluid from leaking out of the rear end of the barrel;

a severable front end wall sealingly temporarily closing the needle receiving chamber of the plunger adjacent the front end thereof to prevent fluid from the fluid chamber from entering the needle receiving chamber;

a needle retaining assembly having an elongated tubular stem with a front end and rear end and having a severable disc member at the rear end thereof sealingly attached to the barrel;

a hollow needle sealingly mounted in the stem at the front end of the barrel and protruding therefrom until fluid has been expelled from the fluid chamber, a rear end of the needle in communication with the fluid chamber to permit the flow of fluid from the fluid chamber through the needle when the plunger is depressed;

a first annular cutting blade member on the front end of the plunger and adapted to sever the disc member on the needle retaining assembly for releasing it from the barrel after the fluid has been expelled from the fluid chamber;

a second annular cutting blade member extending rearwardly from the disc member at the rear end of the needle retaining assembly to sever the front end wall of the plunger and open the front end of the plunger to receive the needle and needle retaining assembly into the needle receiving chamber of the plunger;

both the first and second cutting blade members having a sharp leading edge inclined at an angle to both the front end wall and the severable disc member, so that each leading edge, when severing its respective wall or disc member creates a pointed force and a shearing action to respectively separate either the front end wall from the plunger or the disc from the barrel; and a compression spring within the barrel associated with the needle retaining assembly urging the needle and the needle retaining assembly rearwardly in the barrel and toward a retracted position in the interior of the needle receiving chamber.

19. A safety syringe as claimed in claim 18 wherein the first annular cutting blade member has a large enough inside diameter to telescope over the outside diameter of the second annular cutting blade member and move axially forward with the plunger relative to the second annular cutting blade member to sever the disc member to release the needle retaining assembly from the barrel, and whereupon further forward movement of the plunger, the front end wall of the plunger is moved against the second annular cutting blade member, thereby severing the end wall and creating an end opening thereby permitting the compression spring to move the needle assembly and needle rearwardly through the first annular cutting blade member and then through the end opening into the needle receiving chamber of the plunger.

20. A safety syringe as claimed in claim 18 wherein the compression spring surrounds the stem and is maintained under compression between the severable disc member and a ledge of the barrel.

21. A safety syringe as claimed in claim 18 including a needle hub attached to the front end of the stem and having the needle axially secured therein.

22. A safety syringe as claimed in claim 18 wherein the severable disc has a circular notch, creating a thin membrane and a notch effect, in axial alignment with the first annular cutting blade member to permit the disc to be severed with less pressure of the plunger.

23. A safety syringe as claimed in claim 18 wherein the severable front end wall has a circular notch, creating a thin membrane and a notch effect, to permit the front end wall of the plunger to be severed with less pressure from the plunger.

24. A safety syringe as claimed in claim 18 wherein the compression spring is adapted to retain the needle and needle retaining member within the needle receiving chamber after retraction of the needle.

25. A safety syringe as claimed in claim 18 wherein the angle of inclination of the leading edge of the first and second cutting blade member relative to the front end wall and the severable disc is at least 5°.

26. A safety syringe as claimed in claim 18 wherein the leading edge of both the cutting blade members is inclined at multiple angles.

27. A safety syringe as claimed in claim 18 wherein the axial length of one of the cutting blade members is greater than that of the other to provide sequential rupturing of the first and second rupturable discs.

28. A safety syringe as claimed in claim 27 wherein the first cutting blade member is of greater axial length than the second cutting blade member to sever the disc member before the second cutting blade member severs the front end wall of the plunger.

29. A safety syringe comprising:

a hollow barrel having a cylindrical wall, a rear end opening and a front end opening and a fluid chamber therein extending between said openings;

a hollow plunger mounted in the barrel and axially moveable back and forth within the barrel, for the intake and expulsion of fluid from the barrel, the plunger containing an axial needle receiving chamber therein;

sealing means extending around the plunger, and slidably engaging an inside surface of the wall of the barrel to prevent fluid from leaking out of the rear end of the barrel;

a severable front end wall sealingly closing the needle receiving chamber of the plunger adjacent the front end thereof to prevent fluid from the fluid chamber from entering the needle receiving chamber;

a needle retaining assembly having an axially extending stem member and having a severable disc member extending radially outwardly from the stem member and sealingly attached to the barrel;

a hollow needle sealingly mounted in a needle hub member which is attached to the front end of the stem member and positioned at the front end of the barrel and protruding therefrom until fluid has been expelled from the fluid chamber, a rear end of the needle in communication with the fluid chamber to permit the flow of fluid from the fluid chamber through the needle when the plunger is depressed;

a first annular cutting member on the front end of the plunger and adapted to sever the disc member on the needle retaining assembly for releasing it from the barrel after the fluid has been expelled from the fluid chamber;

a second annular cutting member extending rearwardly from the disc member at the rear end of the needle retaining assembly to sever the front end wall of the plunger and open the front end of the plunger to receive the needle and needle retaining assembly into the needle receiving chamber of the plunger;

both the first and second cutting members having a sharp leading edge inclined at an angle to both the front end wall and the severable disc member, so that each leading edge, when severing its respective wall or disc member creates a pointed force and a shearing action to respectively separate either the front end wall from the plunger or the disc from the barrel; and bias means within the barrel associated with the needle retaining assembly urging the needle and the needle retaining assembly rearwardly in the barrel and toward a retracted position in the interior of the needle receiving chamber.

30. A safety syringe as claimed in claim 29 wherein the first annular cutting member has a large enough inside diameter to telescope over the outside diameter of the second annular cutting member and move axially forward with the plunger relative to the second annular cutting member to sever the disc member to release the needle retaining assembly from the barrel.

31. A safety syringe as claimed in claim 29 wherein the first annular cutting member is integral with the plunger.

32. A safety syringe as claimed in claim 29 wherein the second annular cutting member is integral with the disc member.

33. A safety syringe as claimed in claim 29 wherein an annular barrel recess provides room for the disc member to be ruptured at an annular membrane adjacent to an annular notch by a pointed force and shear action from the first annular cutting member on the front end of the plunger and the annular barrel recess provides room for easier deflection of the disc member to facilitate quick and total rupture of the disc member during a retraction sequence of the needle.

34. A safety syringe as claimed in claim 29 wherein an annular barrel recess provides room for residual medication fluid to avoid accidental spray of the fluid through the needle during retraction.

35. A safety syringe as claimed in claim 29 wherein the plunger has a circumferential protrusion which snaps into the barrel to avoid disengagement of the plunger from the barrel during use.

36. A safety syringe as claimed in claim 35 wherein the protrusion is located substantially near the front end of the plunger and the barrel inside diameter and plunger outside diameter and the diameter of the circumferential protrusion on the plunger is closely matched in dimensions to assure concentricity of the plunger and barrel and proper engagement of each annular cutting member with a respective annular membrane of the front end wall and of the disc member.

37. A safety syringe as claimed in claim 29 wherein the outside diameter of the severable disc member on the stem and the inside diameter of the barrel is dimensionally matched and together with a compressed spring keeps the second annular cutting member concentric with a membrane of the front end wall of the plunger to assure proper severing of the membrane to permit the needle and needle retaining assembly to enter the needle receiving chamber of the hollow plunger.

38. A safety syringe comprising:

a hollow barrel for containing a fluid having a cylindrical wall, a rear end opening and a front end opening and a fluid chamber therein extending between said openings;

a hollow plunger mounted in the fluid chamber of the barrel and axially moveable back and forth between the front and rear end opening of the barrel, for the intake and expulsion of fluid from the fluid chamber, the plunger containing an axial needle receiving chamber therein and the plunger having a rear end portion extending out of the rear end opening of the barrel;

a sealing means extending around the periphery of the plunger, engaging an inside surface of the wall of the barrel within the fluid chamber to prevent fluid from leaking out of the rear end of the barrel;

a barrier means sealingly attached to the plunger adjacent the front end thereof to hydraulically separate the needle receiving chamber from the fluid chamber to prevent fluid from the fluid chamber from entering the needle receiving chamber;

a needle retaining means sealingly attached temporarily to the barrel until fluid has been expelled from the fluid chamber;

a hollow needle sealingly mounted in the needle retaining means and protruding from the front end of the barrel; the fluid chamber being in communication with the interior of the hollow needle to permit fluid to flow from the fluid chamber through the needle when the plunger is moved toward the front end of the barrel;

bias means within the barrel associated with the needle retaining means urging the needle and the needle retaining means rearwardly in the barrel and toward a retracted position in the interior of the needle receiving chamber;

a first annular punch type release means on the front end of the plunger and adapted to rupture the needle retaining means for releasing it from the barrel to permit the bias means to move the needle and needle retaining means toward the needle receiving chamber after the fluid has been expelled from the fluid chamber; and a second annular punch type release means extending rearwardly from the rear end of the needle retaining means to rupture the barrier means and open the front end of the plunger to receive the needle and needle retaining means into the needle receiving chamber.

39. A safety syringe as claimed in claim 38, wherein the needle retaining means is secured to a rear end of the needle and which removably retains the needle in the front end opening of the barrel.

40. A safety syringe as claimed in claim 39, wherein the needle retaining means is a tubular member which has a transversely extending annular flange sealingly engaging the front end of the barrel to insure that all fluid being expelled from the fluid chamber will only pass through the needle as the plunger is depressed.

41. A safety syringe as claimed in claim 38, wherein the barrel has a reduced diameter portion permanently secured to the front end thereof to receive the needle retaining means.

42. A safety syringe as claimed in claim 38, including means to retain the needle in the needle receiving chamber after it has moved into the retracted position.

43. A safety syringe as claimed in claim 38, including a sheath means removably attached to the needle retaining means to cover the needle when in an extended position at the front end of the barrel.

44. A safety syringe as claimed in claim 38, wherein the bias means is a compression spring which is compressed to the greatest extent while the needle is protruding from the front end of the barrel in an extended position and wherein the compression is at least partially relieved when the needle moves into the retracted position within the needle receiving chamber.

45. A safety syringe as claimed in claim 38, wherein the barrier means is a rupturable disk shaped member extending transversely across the plunger adjacent the front end thereof.

* * * * *